United States Patent
Destarac et al.

(10) Patent No.: US 7,285,610 B2
(45) Date of Patent: Oct. 23, 2007

(54) SYNTHESIS METHOD FOR POLYMERS BY CONTROLLED RADICAL POLYMERISATION WITH XANTHATES

(75) Inventors: Mathias Destarac, Paris (FR); Dominique Charmot, Los Gatos, CA (US); Samir Zard, Gif sur Yvette (FR); Isabelle Gauthier-Gillaizeau, Carquefou (FR)

(73) Assignee: Rhodia Chimie, Aubervilliers (FR)

( * ) Notice: Subject to any disclaimer, the term of this patent is extended or adjusted under 35 U.S.C. 154(b) by 422 days.

(21) Appl. No.: 10/941,954

(22) Filed: Sep. 16, 2004

(65) Prior Publication Data

US 2005/0054794 A1   Mar. 10, 2005

Related U.S. Application Data

(62) Division of application No. 10/149,063, filed as application No. PCT/FR00/03458 on Dec. 8, 2000, now Pat. No. 6,809,164.

(30) Foreign Application Priority Data

Dec. 9, 1999   (FR) .................................. 99 15555

(51) Int. Cl.
*C08F 4/00* (2006.01)
(52) U.S. Cl. .................. 526/193; 526/213; 526/214; 526/222; 526/307.7; 526/318; 526/318.3; 526/319
(58) Field of Classification Search ............. 526/193, 526/213, 214, 222, 307.7, 318, 318.3, 319
See application file for complete search history.

(56) References Cited

U.S. PATENT DOCUMENTS

| 3,901,932 A | 8/1975 | Tutomu et al. |
| 5,194,539 A | 3/1993 | Charmot et al. |
| 6,124,382 A | 9/2000 | Corpart et al. |
| 6,153,705 A | 11/2000 | Corpart et al. |
| 6,569,969 B2 | 5/2003 | Charmot et al. |

FOREIGN PATENT DOCUMENTS

| FR | 2 764 892 | 12/1998 |
| WO | WO 98/01478 | 1/1998 |
| WO | WO 98/58974 | 12/1998 |
| WO | WO 00/75207 | 12/2000 |

OTHER PUBLICATIONS

Burke, Jr., T.R. et al., *J. Org. Chem.*, vol. 58, No. 6, pp. 1336-1340, XP002141808 (1993).
Burke, Jr., T.R., et al., *Med. Chem.*, vol. 34, No. 5, pp. 1577-1581, XP002141809 (1991).
Database, Chem. Abstracts, F. Tada et al., Abstract No. XP002141811 & JP 50 111106 (Sakai Chemistry Industry Co., Ltd. Japan), Sep. 1, 1975.
Anderson, G.T., et al., J. Org. Chem., vol. 61, No. 1, pp. 125-132, XP002141810, (1996).

*Primary Examiner*—Helen L Pezzuto
(74) *Attorney, Agent, or Firm*—Buchanan, Ingersoll & Rooney, PC

(57) ABSTRACT

A polymer composition and method of preparing same is described wherein an ethylenically unsaturated monomer is contacted with a source of free radicals and a compound of formula (1A), (1B) and (1C) as defined herein. The polymer composition may be a homopolymer or a block copolymer.

3 Claims, No Drawings

SYNTHESIS METHOD FOR POLYMERS BY CONTROLLED RADICAL POLYMERISATION WITH XANTHATES

CROSS-REFERENCE TO RELATED APPLICATIONS

This applications is a divisional of application Ser. No. 10/149,063, filed Jun. 7, 2002, now U.S. Pat. No. 6,809,164, which is a 371 of International Application No. PCT/FR00/03458, filed Dec. 8, 2000, and which, in turn, claims priority from French Patent Application No. 99/15555, filed Dec. 9, 1999, which applications are hereby incorporated by reference in their entirety.

The present invention relates to a novel method for "controlled" or "live" radical polymerisation leading to polymers, especially block copolymers.

Block polymers are normally prepared by ionic polymerisation. That type of polymerisation has the disadvantage of permitting the polymerisation of only specific types of non-polar monomer, especially styrene and butadiene, and of requiring a particularly pure reaction medium and temperatures often lower than the ambient temperature in order to minimise parasitic reactions, thus giving rise to major implementation constraints.

Radical polymerisation has the advantage of being easy to implement without respecting excessive conditions of purity and at temperatures equal to or higher than the ambient temperature. However, until recently, there was no radical polymerisation method enabling block polymers to be obtained.

Since then, a novel radical polymerisation method has been developed: the method involved is so-called "controlled" or "live" radical polymerisation. Radical polymerisation proceeds by growth by propagation of macro-radicals. Those macro-radicals, which have a very short life, recombine irreversibly by coupling or dismutation. When polymerisation takes place in the presence of several comonomers, the variation in the composition of the mixture is extremely slight considering the life of the macro-radical, so that the chains have a random chain formation from the monomer units and not a block chain formation.

Recently, techniques for controlled radical polymerisation have been developed in which the ends of polymer chains can be reactivated into the form of a radical by homolytic bond cleavage (for example C—O, or C-Halogen).

Controlled radical polymerisation therefore has the following distinctive aspects:
1. The number of chains is fixed throughout the duration of the reaction,
2. The chains all grow at the same rate, which translates into:
   a linear increase in the molar masses with the conversion,
   a narrow mass distribution,
3. The average molar mass is controlled by the molar ratio of the monomer to the chain precursor,
4. The possibility of preparing block copolymers.

The controlled character is all the more marked because the rate of reactivation of the chains into radical form is very high considering the rate of growth of the chains (propagation). There are cases in which this is not always true (i.e. the rate of reactivation of the chains into: radical form is higher than or equal to the rate of propagation) and conditions 1 and 2 are not observed. Nevertheless, it is still possible to prepare block copolymers.

WO 98/58974 describes a live radical polymerisation method enabling block copolymers to be obtained by a method without UV irradiation, by using xanthate compounds, the properties of which are:

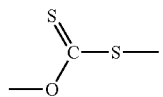

That radical polymerisation enables block polymers to be prepared in the absence of a UV source, using any type of monomer. The polymers obtained do not contain metallic impurities which would militate against their use. They are functionalised at the end of the chain and have a low index of polydispersion of less than 2 and even less than 1.5.

One object of the present invention is to propose a novel polymerisation method using novel precursors of the xanthate type.

Another object is to propose a polymerisation method using precursors of the xanthate type, in the course of which the number-average molar masses $M_n$ of the polymers obtained are well controlled, that is to say, close to the theoretical values $M_{n,th}$, this being throughout the polymerisation reaction.

Another object is to propose a polymerisation method using precursors of the xanthate type for the synthesis of block copolymers and homopolymers having a polydispersion index ($M_w/M_n$) which is low, that is to say, close to 1.

The work of the inventors has resulted in a method for radical polymerisation in which block copolymers or homopolymers can be prepared in accordance with a process having remarkable and substantially greater control than the methods known hitherto.

This method uses xanthates of a particular type which themselves constitute novel molecules.

The invention therefore relates to a method for the preparation of polymers, characterised in that there are brought into contact with one another:
  at least one ethylenically unsaturated monomer,
  at least one source of free radicals, and
  at least one compound (I) of the general formula (IA), (IB) or (IC):

(IA)

(IB)

(IC)

in which:
R² and R²', which may be identical or different, represent a group of the formula:

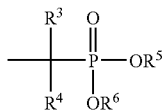

in which:
R³ and R⁴, which may be identical or different, are selected from a halogen group, —NO₂, —SO₃R, —NCO, CN, R, —OR, —SR, —NR₂, —COOR, O₂CR, —CONR₂, —NCOR₂, $C_nF_{2n+1}$ with n being 1 to 20, preferably 1,
in which the groups R, which may be identical or different, represent H or a group selected from:
alkyl,
alkenyl,
alkynyl,
cycloalkenyl,
cycloalkynyl,
aryl, optionally fused to an aromatic or non-aromatic heterocycle,
alkaryl,
aralkyl,
heteroaryl,
which are optionally substituted by one or more identical or different groups selected from halogen, =O, =S, OH, alkoxy, SH, thioalkoxy, NH₂, mono- or di-alkylamino, CN, COOH, ester, amide, $C_nF_{2n+1}$ (n being 1 to 20), and/or optionally interrupted by one or more atoms selected from O, S, N, P,
or a heterocyclic group optionally substituted by one or more groups such as defined above,
or R³ and R⁴, together with the carbon atom to which they are attached, form a group =O or =S or a hydrocarbon ring or a heterocycle,
R⁵ and R⁶, which may be identical or different, represent a group such as defined above for R,
or R⁵ and R⁶ together form a $C_2$-$C_4$ hydrocarbon chain optionally interrupted by a hetero atom selected from O, S, N and P,
R¹ and R¹', which may be identical or different, represent a group such as defined above for R³ or R⁴,
p represents an integer from 2 to 10.

According to the invention, the term "alkyl" denotes a linear or branched hydrocarbon radical containing from 1 to 20 carbon atoms, such as methyl, ethyl, propyl, isopropyl, butyl, tert-butyl, isobutyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl.

"Alkenyl" means a linear or branched hydrocarbon chain of from 2 to 20 carbon atoms comprising one or more double bonds. Examples of particularly preferred alkenyl groups are alkenyl groups carrying a single double bond, such as —CH₂—CH₂—CH=C(CH₃)₂, vinyl or allyl.

"Alkynyl" means a linear or branched hydrocarbon chain of from 2 to 20 carbon atoms comprising one or more triple bonds. Examples of particularly preferred alkynyl groups are alkynyl groups carrying a single triple bond, such as —CH₂—CH₂—C≡CH.

The term "cycloalkyl" denotes saturated hydrocarbon groups which may be monocyclic or polycyclic and which comprise from 3 to 12 carbon atoms, preferably from 3 to 8 carbon atoms. Monocyclic cycloalkyl groups, such as cyclopropyl, cyclobutyl, cyclopentyl, cyclohexyl, cycloheptyl, cyclooctyl, cyclononyl, cyclodecyl, cycloundecyl and cyclododecyl are more particularly preferred.

According to the invention, "cycloalkenyl" means a group derived from a cycloalkyl group as defined above, having one or more double bonds, preferably one double bond.

According to the invention, "cycloalkynyl" means a group derived from a cycloalkyl group as defined above, having one or more triple bonds, preferably one triple bond.

The term "aryl" represents an aromatic monocyclic or bicyclic hydrocarbon group comprising from 6 to 10 carbon atoms, such as phenyl or naphthyl.

"Alkaryl" means an aryl group as defined above, substituted by an alkyl group.

"Aralkyl" means an alkyl group as defined above, substituted by an aryl group.

"Alkoxy" means an O-alkyl group generally having from 1 to 20 carbon atoms, especially methoxy, ethoxy, propoxy and butoxy.

"Halogen" means a fluorine, chlorine, bromine or iodine atom.

When the alkyl group is optionally halogenated, it preferably represents perfluoroalkyl and especially pentafluoroethyl or trifluoromethyl.

The term "heteroaryl" denotes aromatic groups which are monocyclic with from 5 to 7 chain members or bicyclic with from 6 to 12 chain members and which comprise one, two or three endocyclic hetero atoms selected from O, N and S. Examples thereof are the groups furyl, thienyl, pyrrolyl, oxazolyl, isoxazolyl, thiazolyl, isothiazolyl, imidazolyl, pyrazolyl, oxadiazolyl, triazolyl, thiadiazolyl, pyridyl, pyridazinyl, pyrazinyl and triazinyl.

Preferred heteroaryls comprise 4 or 5 carbon atoms and 1 or 2 hetero atoms.

The term heterocyclic group denotes monocyclic or bicyclic saturated or preferably unsaturated carbon rings having from 5 to 12 chain members and 1, 2 or 3 endocyclic hetero atoms selected from O, N and S. These are generally derivatives of the heteroaryl groups described above.

Preferably, when it is unsaturated, the heterocycle comprises a single double bond. Preferred examples of unsaturated heterocycles are dihydrofuryl, dihydrothienyl, dihydropyrrolyl, pyrrolinyl, oxazolinyl, thiazolinyl, imidazolinyl, pyrazolinyl, isoxazolinyl, isothiazolinyl, oxadiazolinyl, pyranyl and the mono-unsaturated derivatives of piperidine, of dioxane, of piperazine, of trithiane, of morpholine, of dithiane, of thiomorpholine, and also tetrahydropyridazinyl, tetrahydropyrimidinyl and tetrahydrotriazinyl.

When one of the above groups represents an aryl group optionally fused to an unsaturated heterocycle, the unsaturated heterocycle has from 5 to 7 chain members and preferably a single unsaturation in common with the aryl group.

The method according to the invention therefore consists in bringing into contact with one another a source of free radicals, an ethylenically unsaturated monomer and a compound (I) of formula (IA), IB) or (IC).

The compound (I) carries a xanthate function. According to the essential feature of the invention, the xanthate function carries a group R² or R²' which is substituted by a group P(O)(OR⁵)(OR⁶) such as defined above.

Advantageously, the group R³ is an electron-attracting group.

According to a preferred variant, R² represents a group such as defined above and R³ represents an alkyl group substituted by at least one fluorine, chlorine and/or bromine atom. The preferred groups $R^3$ are the following:

$CF_3$
$CF_2CF_2CF_3$
$C_6F_{16}$,

According to another preferred variant, $R^3$ represents a group CN or $NO_2$.

Advantageously, $R^4$ represents a hydrogen atom. The groups $R^5$ and $R^6$ preferably represent a linear, branched or cyclic alkyl group advantageously containing from 1 to 20 carbon atoms.

There may be mentioned, in particular, the groups methyl, ethyl, isopropyl, propyl, butyl, isobutyl, tert-butyl, pentyl, n-pentyl, hexyl, cyclohexyl, heptyl, ethylhexyl, octyl, nonyl, decyl, undecyl, dodecyl, tridecyl, tetradecyl, hexadecyl, octadecyl.

Those groups may be present in the various possible isomeric forms.

$R^5$ and $R^6$ may also represent a substituted alkyl group comprising one or more identical or different substituents. There may be mentioned, in particular, the substituting groups acyl, such as acetyl; alkoxy, such as methoxy, butoxy, phenyloxy, cyclohexyloxy; halo, especially chloro and fluoro; hydroxy; aryl, such as phenyl and naphthalenyl; aralkyl; alkenyl, especially hexenyl, cyclohexenyl and propenyl.

A particularly advantageous sub-group is constituted by alkyl groups substituted by one or more halogen atoms, preferably fluorine atoms, the group $C_nF_{(2n+1)}$—$CH_2$ (n being as defined above) being particularly preferred.

$R^5$ and $R^6$ may also together form a cyclic group comprising a phosphorus atom, for example a group

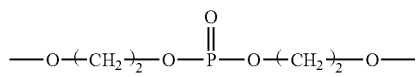

The most valuable results were obtained for the compound (I) when $R^1$ is a group selected from:

$CH(CH_3)(CO_2Et)$
$CH(CH_3)(C_6H_5)$
$CH(CO_2Et)_2$
$C(CH_3)(CO_2Et)(S-C_6H_5)$
$C(CH_3)_2(C_6H_5)$, et

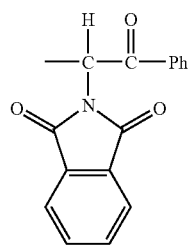

in which Et represents an ethyl group and Ph represents a phenyl group.

The groups $R^1$ and $R^{1'}$ may also represent a polymer chain resulting from radical or ionic polymerisation or resulting from polycondensation. Preferred compounds of formula (IC) are those in which $R^{1'}$ is the group —$CH_2$-phenyl-$CH_2$— or the group —$CHCH_3CO_2CH_2CH_2CO_2CHCH_3$—.

$R^2$ is preferably a group:

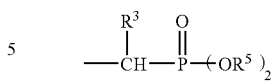

in which $R^3$ is $CF_3$, $CF_2CF_2CF_3$, $C_6F_{13}$ or CN and $R^5$ is a $C_1$-$C_4$ alkyl group, preferably ethyl.

According to the preferred form of the invention, the polymerisation method uses a compound (I) of formula (IA). The preferred compounds of formula (IA) are the following:

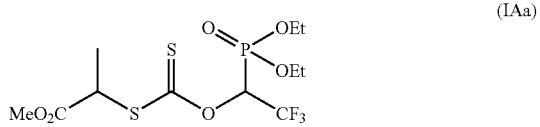

(IAa)

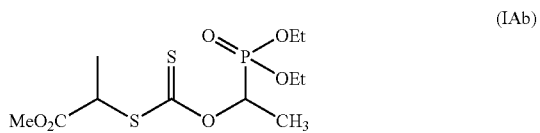

(IAb)

The compounds of formula (IA) may, in particular, be obtained by:

a) reacting a carbonyl compound of the general formula II:

(II)

$R^3$ and $R^4$ being as defined above, with a phosphite of the general formula III:

(III)

$R^5$ and $R^6$ being as defined above, to form a compound of the general formula IV:

(IV)

$R^3$, $R^4$, $R^5$ and $R^6$ being as defined above, b) reacting the compound of formula IV with carbon disulphide $CS_2$ in the presence of a metal alcoholate $M^+OR^{1'-}$ to yield a xanthate of formula V:

$R^2O$ (C=S)—$S^-$, $M^+$ (V)

in which $R^2$ is as defined above and M represents a cation, especially an alkali metal cation;

c) reacting the compound of formula V with a compound of formula VI:

 (VI)

in which $R^1$ is as defined above and X-represents a halogen atom, to yield the compound of formula (IA) as defined above.

The compounds of the general formula IB are obtained in the same manner starting from polyhydroxylated compounds corresponding to the alcohol of the general formula IV.

The compounds of the general formula IC are obtained in the same manner starting from the polyhalogenated analogue of the alkyl halide of the general formula VI.

The compounds of the general formula II are commercially available or can be readily prepared by the person skilled in the art using conventional procedures.

The phosphites of the general formula III can thus be prepared by reaction between an alcohol and $PCl_3$ in a manner known to the person skilled in the art. When the groups $R^5$ and/or $R^6$ have a high carbon number, it is preferable first of all to prepare phosphites having a low molecular weight, for example a diethyl phosphite, and then, by a transesterification route, to replace the ethoxy groups by alkoxy groups having a higher molecular weight.

In the case of aromatic phosphites, it is preferred first of all to prepare triphenyl phosphite and to react it with phosphorous acid to obtain diphenyl phosphite.

The following phosphites may also be prepared:
dimethyl phosphite
diethyl phosphite
dipropyl phosphite
dibutyl phosphite
dipentyl phosphite
dihexyl phosphite
diheptyl phosphite
dioctyl phosphite
dinonyl phosphite
didecyl phosphite
diundecyl phosphite
didodecyl phosphite
ditridecyl phosphite
ditetradecyl phosphite
dihexadecyl phosphite
dioctadecyl phosphite
bis[2-(acetyloxy)ethyl]phosphite
bis(4-butoxybutyl)phosphite
bis[2-(cyclohexyloxy)methylethyl]phosphite
bis(methoxymethyl)phosphite
bis[2-chloro-1-(chloromethyl)ethyl]phosphite
bis(2-chloroethyl)phosphite
bis(2-chloropropyl)phosphite
bis(2,3-dihydroxypropyl)phosphite
bis(2-hydroxyethyl)phosphite
bis(2,2,3,3,4,4,5,5,6,6,7,7-dodecafluoroheptyl)phosphite
bis(2-fluoroethyl)phosphite
bis(2,2,3,3,4,4,5,5-octafluoropentyl)phosphite
bis(2,2,3,3-tetrafluoropropyl)phosphite
bis(2,2,2-trifluoroethyl)phosphite
2,2,3,3,4,4,5,5,6,6,7,7-dodecafluoroheptylmethyl phosphite
methyl 2,2,3,3,4,4,5,5-octafluoropentyl phosphite
methyl 2,2,3,3-tetrafluoropropyl phosphite
diphenyl phosphite
bis(4-methylphenyl)phosphite
bis(4-nonylphenyl)phosphite
di-1-naphthalenyl phosphite
dicyclohexyl phosphite
di-2-cyclohexen-1-yl phosphite
di-2-propenyl phosphite
2,7-dioxo(2,7-H)-1,3,6,8-tetraoxa-2,7-diphosphocyclodecane In the same manner as indicated above, it is possible to prepare phosphites in which $R^5$ and $R^6$ are different, starting from the corresponding compounds of different alcohols.

According to the method of the invention, the source of free radicals is generally a radical polymerisation initiator. However, in the case of some monomers, such as styrene, thermal initiation is sufficient to generate free radicals.

In the first case, the radical polymerisation initiator may be selected from the initiators conventionally used in radical polymerisation. It may be, for example, one of the following initiators:

hydrogen peroxides, such as: t-butyl hydroperoxide, cumene hydroperoxide, t-butyl peroxyacetate, t-butyl peroxybenzoate, t-butyl peroxyoctoate, t-butyl peroxyneodecanoate, t-butyl peroxyisobutyrate, lauroyl peroxide, t-amyl peroxypivalate, t-butyl peroxypivalate, dicumyl peroxide, benzoyl peroxide, potassium persulphate, ammonium persulphate, azo compounds, such as: 2,2'-azo-bis(isobutyronitrile), 2,2'-azo-bis(2-butyronitrile), 4,4'-azo-bis(4-pentanoic acid), 1,1'-azo-bis(cyclohexanecarbonitrile), 2-(t-butylazo)-2-cyanopropane, 2,2'-azo-bis[2-methyl-N-(1,1)-bis(hydroxymethyl)-2-hydroxyethyl]propionamide, 2,2'-azo-bis(2-methyl-N-hydroxyethyl]propionamide, 2,2'-azo-bis(N,N'-dimethyleneisobutyramidine)dichloride, 2,2'-azo-bis(2-amidinopropane)dichloride, 2,2'-azo-bis(N,N'-dimethyleneisobutyramide), 2,2'-azo-bis(2-methyl-N-[1,1-bis(hydroxymethyl)-2-hydroxyethyl]propionamide), 2,2'-azo-bis(2-methyl-N-[1,1-bis(hydroxymethyl)ethyl]propionamide), 2,2'-azo-bis[2-methyl-N-(2-hydroxyethyl)propionamide], 2,2'-azo-bis(isobutyramide)dihydrate, redox systems comprising combinations such as:

mixtures of hydrogen peroxide, alkyl peroxide, peresters, percarbonates and the like and of any one of the salts of iron, titanium salts, zinc formaldehydesulphoxylate or sodium formaldehydesulphoxylate, and reducing sugars, the persulphates, perborate or perchlorate of alkali metals or of ammonium in association with an alkali metal bisulphite, such as sodium metabisulphite, and reducing sugars, alkali metal persulphates in association with an arylphosphinic acid, such as benzenephosphonic acid and the like, and reducing sugars.

The quantity of initiator to be used is generally determined in such a manner that the quantity of radicals generated is a maximum of 20 mol. % relative to the quantity of compound (II), preferably a maximum of 5 mol. %.

According to the method of the invention, the ethylenically unsaturated monomers are more especially selected from styrene and its derivatives, butadiene, chloroprene, (meth)acrylic esters, vinyl esters and vinyl nitriles.

(Meth)acrylic esters means esters of acrylic acid and methacrylic acid, respectively, with hydrogenated or fluorinated $C_1$-$C_{12}$, preferably $C_1$-$C_8$, alcohols. Of the alcohols of that type there may be mentioned: methyl acrylate, ethyl acrylate, propyl acrylate, n-butyl acrylate, isobutyl acrylate, 2-ethylhexyl acrylate, t-butyl acrylate, methyl methacrylate, ethyl methacrylate, n-butyl methacrylate, isobutyl methacrylate.

Vinyl nitrites include, more especially, those having from 3 to 12 carbon atoms, such as, in particular, acrylonitrile and methacrylonitrile.

It should be noted that styrene may be replaced completely or partially by derivatives, such as alphamethylstyrene or vinyltoluene.

Other ethylenically unsaturated monomers, which may be used alone or in admixture, or which are copolymerisable with the above monomers are especially:

- carboxylic acid vinyl esters, such as vinyl acetate, vinyl Versatate®, vinyl propionate,
- vinyl halides,
- ethylenically unsaturated mono- and di-carboxylic acids, such as acrylic acid, methacrylic acid, itaconic acid, maleic acid, fumaric acid and the mono-alkyl esters of dicarboxylic acids of the type mentioned with alkanols preferably having from 1 to 4 carbon atoms and their N-substituted derivatives,
- amides of unsaturated carboxylic acids, such as acrylamide, methacrylamide, N-methylolacrylamide or N-methylolmethacrylamide, N-alkylacrylamides,
- ethylenically unsaturated monomers comprising a sulphonic acid group and its alkali or ammonium salts, for example vinylsulphonic acid, vinylbenzenesulphonic acid, alpha-acrylamidomethylpropanesulphonic acid, 2-sulphoethylene methacrylate,
- vinylamine amides, especially vinylformamide or vinylacetamide,
- ethylenically unsaturated monomers comprising a secondary, tertiary or quaternary amino group, or a heterocyclic group containing nitrogen, such as, for example, vinylpyridines, vinylimidazole, aminoalkyl (meth)acrylates and aminoalkyl (meth)acrylamides, such as dimethylaminoethyl acrylate or methacrylate, di-tert-butylaminoethyl acrylate or methacrylate, dimethylaminomethylacrylamide or dimethylaminomethylmethacrylamide. It is also possible to use zwitterionic monomers, such as, for example, sulphopropyl(dimethyl)aminopropyl acrylate.

For the preparation of polyvinylamines, it is preferable to use vinylamine amides, for example vinylformamide or vinylacetamide, as ethylenically unsaturated monomers. The polymer obtained is then hydrolysed at an acid or basic pH.

For the preparation of polyvinyl alcohols, it is preferable to use carboxylic acid vinyl esters, such as, for example, vinyl acetate, as ethylenically unsaturated monomers. The polymer obtained is then hydrolysed at an acid or basic pH.

The types and amounts of polymerisable monomers used according to the present invention vary in accordance with the particular final application for which the polymer is intended. Those variations are well known and can be readily determined by the person skilled in the art.

The polymerisation can be carried out in bulk, in solution or in emulsion. It is preferably implemented in emulsion.

Preferably, the method is implemented in a semi-continuous manner.

The temperature may vary from ambient temperature to 150° C. depending on the nature of the monomers used.

In general, in the course of polymerisation, the instantaneous content of polymer relative to the instantaneous amount of monomer and polymer is from 50 to 99% by weight, preferably from 75 to 99%, and even more preferably from 90 to 99%. That content is maintained in known manner by controlling the temperature and the rate of addition of the reagents and optionally the polymerisation initiator.

Generally, the method is implemented in the absence of a UV source.

The method according to the invention has the advantage of permitting the control of the number-average molar masses $M_n$ of the polymers. Thus, those masses $M_n$ are close to the theoretical values $M_{n\,th}$, $M_{n\,th}$ being expressed by the following formula:

$$M_{n\,th} = \frac{[M]_0}{[P]_0} \frac{X}{100} M_0$$

in which:

[M]$_0$ represents the initial molar concentration of monomer;

[P]$_0$ represents the initial concentration of precursor compound;

X represents the conversion of the monomer expressed as a percentage;

$M_0$ represents the molar mass of the monomer (g/mol).

According to the present invention, the control of Mn is visible at the beginning of polymerisation and remains present during the progress of the reaction.

In addition, the polymerisation method according to the present invention leads to polymers having a low index of polydispersion (Ip=$M_w/M_n$ with $M_w$: weight-average molar mass) close to 1.

The invention therefore relates also to compositions which can be obtained by the method described above which consists in bringing into contact with one another at least one ethylenically unsaturated monomer, at least one source of free radicals and at least one compound of formula (IA), (IB) or (IC).

Generally, those polymer compositions have a polydispersion index of at most 2, preferably at most 1.5.

The invention relates also to a composition comprising predominantly a polymer of the general formula (IIIa):

$$\underset{R^2-O}{\overset{S}{\underset{\|}{C}}}-S-\left[\underset{Y'}{\overset{Y}{\underset{|}{C}}}-(CW=CW')_a-CH_2\right]_m\left[\underset{X'}{\overset{X}{\underset{|}{C}}}-(CV=CV')_b-CH_2\right]_n R^1 \quad \text{(IIIA)}$$

in which:

R¹ and R² are as defined above;

V, V', W and W', which may be identical or different, represent H, an alkyl group or halogen;

X, X' Y and Y', which may be identical or different, represent H, a halogen or a group $R^7$, $OR^7$, $O_2COR^7$, NHCOH, OH, $NH_2$, $NHR^7$, $NR_2$, $R_2N^+O^-$, $NHCOR^7$, $CO_2H$, $CO_2R^7$, CN, $CONH_2$, $CONHR^7$ or $CONR_2$, in which $R^7$ is as defined above for R, a and b, which may be identical or different, are 0 or 1;

m and n, which may be identical or different, are higher than or equal to 1, and when one or the other is higher than 1, the repeating units are identical or different.

The invention relates more especially to a composition comprising a homopolymer of the general formula (IIIA) as defined above in which the repeating units are identical, or a block copolymer of the general formula (IIIA) as defined above in which the repeating units are different.

The block polymers result from bringing into contact with one another:

an ethylenically unsaturated monomer of the formula:

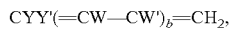

a precursor polymer of the general formula (IIA):

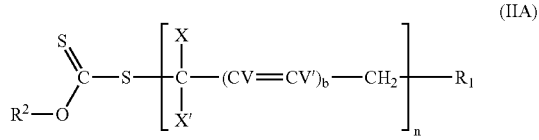

and a source of free radicals.

The invention relates in particular to block polymers which have at least two polymer blocks selected from the following associations:

polystyrene/poly(methyl acrylate),
polystyrene/poly(ethyl acrylate),
polystyrene/poly(tert-butyl acrylate),
poly(ethyl acrylate)/poly(vinyl acetate),
poly(butyl acrylate)/poly(vinyl acetate),
poly(tert-butyl acrylate)/poly(vinyl,acetate).

The invention relates also to a method for the preparation of multi-block block polymers in which the implementation of the polymerization method described above is repeated at least once, using:

monomers differing from those used in the previous implementation, and instead of the compound (I) of formula (IA), (IB) or (IC), the polymer resulting from the previous implementation, which is called the precursor polymer.

The complete method for the synthesis of a block polymer according to the invention may therefore consist in:

(1) synthesising a precursor polymer by bringing into contact with one another an ethylenically unsaturated monomer, a source of free radicals and a compound of formula (IA), (IB) or (IC), (2) using the precursor polymer obtained in step (1) to prepare a di-block block polymer by bringing that precursor polymer into contact with a fresh ethylenically unsaturated monomer and a source of free radicals.

Step (2) may be repeated as many times as desired with fresh monomers in order to synthesise new blocks and thus to obtain a multi-block block polymer.

If the implementation is repeated once more, a tri-block block polymer is obtained and if it is repeated a second time, a "quadriblock" block polymer is obtained, and so on. Thus, at each fresh implementation, the product obtained is a block polymer having an additional polymer block.

For the preparation of multi-block block polymers, the method consists in repeating the implementation of the previous method several times on the block polymer resulting from each previous implementation with different monomers.

The compounds of formula (IB) and (IC) are particularly valuable because they enable a polymer chain to be grown on at least two active sites. With that type of compound, it is possible to cut out polymerisation steps to obtain a copolymer having n blocks. Thus, if p equals 2 in formula (IB) or (IC), the first block is obtained by polymerising a monomer M1 in the presence of the compound of formula (IB) or (IC). That first block can then grow at each of its ends by polymerisation with a second monomer M2 to form a tri-block copolymer. The tri-block polymer can itself grow at each of its ends by polymerisation with a third monomer M3 to form a "pentablock" copolymer in only three steps. If p is higher than 2, the method enables block copolymers or homopolymers to be obtained, the structure of which is "multi-armed" or hyper-branched.

According to this method for the preparation of multi-block polymers, when it is desired to obtain block polymers that are homogeneous and that do not have a composition gradient, and if all of the successive polymerisations are carried out in the same reactor, it is vital that all of the monomers used in a step have been consumed before the polymerisation of the following step commences and, therefore, before the fresh monomers are introduced.

As in the case of the method for the polymerisation of monoblock polymers, this method for the polymerisation of block polymers has the advantage of leading to block polymers having a low polydispersion index. It also enables the molar mass of the block polymers to be controlled.

The following Examples illustrate the invention without, however, limiting the scope thereof.

EXAMPLE 1

Preparation of 2-[1-diethoxyphosphoryl)-2,2,2-trifluoroethoxythiocarbonylsulphanyl)-propionic acid ethyl ester (xanthate IAa)

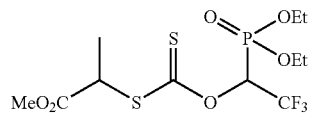

Synthesis of 2,2,2-trifluoro-1-hydroxyethylphosphonic acid diethyl ester (alcohol IVa)

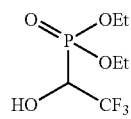

A solution of fluoral hydrate (10 g, 75% aqueous solution, 64.6 mmol) and of diethyl phosphite HP(O)(OEt)₂ (64.6 mmol) in triethylamine (9 ml, 64.6 mmol) is agitated at ambient temperature for 15 hours. After rapid evaporation under reduced pressure (bath temperature lower than or equal to 40° C.), the liquid residue is purified by flash chromatography (petrol/acetone 10:1 then pure ether and ether/methanol 10:1) to give the desired compound IVa with a yield of 82%.

IR (film) 3400, 2992, 2918, 1640, 1268 cm$^{-1}$; MS (IC) m/z 237 [MH]$^+$; $^1$H NMR (200 MHz, CDCl$_3$) δ 6.08 (sl, 1H), 4.12-4.38 (m, 5H), 1.33 (t, J=7.1 Hz, 3H).

Synthesis of 2-[1-diethoxyphosphoryl)-2,2,2-trifluoro-ethoxythiocarbonylsulphanyl)-propionic acid ethyl ester (xanthate IAa)

A solution of 5 g (21.18 mmol) of alcohol IVa in DMF (6 ml) is added dropwise to a suspension of NaH (1.03 g, 60% in dispersion in oil, 25.75 mmol) in DMF. (30 ml) cooled to 0° C. After 30 minutes at 0° C., 2.65 ml (44 mmol) of CS$_2$ are added, agitation is maintained for 15 minutes and then 3.51 ml (26.7 mmol) of ethyl-2-bromopropionate are added. The mixture is left at 0° C. for 23 hours, then neutralised by the addition of a saturated solution of NH$_4$Cl, extracted with ethyl acetate (3 times) and then dried over MgSO$_4$. After evaporation of the solvents and purification by flash chromatography (silica, petrol/ethyl acetate 9:1), xanthate IAa is isolated with a yield of 21%.

IR (film) 2982, 2931, 1736, 1450, 1158 cm$^{-1}$; MS (IC) m/z [MH]$^+$; $^1$H NMR (MHz, CDCl$_3$) δ 4.03-4.37 (m, 7H), 1.75 (d, J=6.8 Hz, 3H), 1.20-1.56 (m, 9H); $^{13}$C NMR (50 MHz, CDCl$_3$) δ 198.0, 170.3, 64.8, 64.7, 61.9, 40.2, 28.4, 15.9, 15.8, 13.8.

EXAMPLE 2

Preparation of 2-[1-diethoxyphosphoryl)-ethoxythiocarbonylsulphanyl)-propionic acid ethyl ester (xanthate IAb)

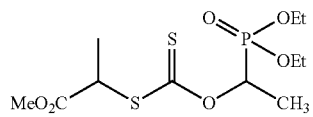

2.07 ml (16.13 mmol) of diethyl phosphite HP(O)(OEt)$_2$ are added dropwise to a suspension of NaH (645 mg, 60% in dispersion in oil) in THF (30 ml) cooled to −78° C. The reaction mixture is agitated at −78° C. for 40 minutes, then at 0° C. for 30 minutes. At that temperature, 847 μl (15.16 mmol) of acetaldehyde are then added and the mixture is allowed to return to ambient temperature for 2 hours 30 minutes. 4.8 ml (80.64 mmol) of CS$_2$ are then added and, after 30 minutes at 0° C., 2.08 ml (16.02 mmol) of ethyl 2-bromopropionate are added. Agitation is maintained for a further 30 minutes and then the reaction mixture is neutralised by the addition of a saturated NH$_4$Cl solution, extracted with ethyl acetate (3 times) and then dried over MgSO$_4$. After evaporation of the solvents and purification by flash chromatography (silica, heptane/ethyl acetate 2:8 then pure ethyl acetate), the xanthate IAb is isolated with a yield of 30%.

IR (film) 2983, 2935, 1736, 1641, 1213, 1040 cm$^{-1}$; MS (IC) m/z 359 [MH]$^+$; $^1$H NMR (200 MHz, CDCl$_3$) δ 4.11-4.26 (m, 8H), 1.52-1.63 (m, 6H), 1.26-1.39 (m, 9H); $^{13}$C NMR (50 MHz, CDCl$_3$) δ 198.0, 170.9, 74.6, 74.5, 71.9, 71.8, 63.2, 63.1, 63.0, 62.9, 61.8, 47.9, 47.6, 17.1, 16.9, 16.5; 16.4, 14.6, 14.1.

EXAMPLE 3

Polymerisation of Ethyl Acrylate in the Presence of Xanthate IAa(I)

There are introduced into a Carius tube:

3.6×10$^{-3}$ mmol of azo-bis-isobutyronitrile (AIBN) (0.6 mg), 10 mmol of ethyl acrylate (1 g)

0.12 mmol of xanthate IAa (51.5 mg)

1.08 cm$^3$ of toluene.

The tube is connected to a vacuum manifold, immersed in liquid nitrogen and then three cycles of "freezing/vacuum/return to ambient" are carried out on the contents of the tube in order to degas it. It is then sealed under vacuum. After returning to ambient, it is immersed in an oil bath preheated to 80° C. The tube is removed from the oil bath after 8 hours and is immersed in liquid nitrogen in order to stop the polymerisation and to be analysed. The polymer is recovered by opening the tube and then evaporating the traces of residual monomer.

A check is carried out on:

conversion into monomer by gravimetry conversion into xanthate (by GPC, UV detection)

$M_n$ and $M_w/M_n$ by GPC.

The conversion into monomer is 88.4%.

The conversion into xanthate is 100%.

$M_n$ equals 7300 g/mol.

$M_w/M_n$ equals 1.18.

By way of comparison, a reaction carried out under the same initial conditions of temperature and concentration, the xanthate of the prior art (ethyl a-(O-ethylxanthyl) propionate) (or O-ethyl S-(1-methoxycarbonylethyl)dithiocarbonate) leads to a polymer having a polydispersion index close to 1.80.

EXAMPLE 4

Polymerisation of Styrene in the Presence of Xanthate IAa (II)

There are introduced into a Carius tube:

14.4 mmol of styrene (1.5 g)

0.18 mmol of xanthate IAa (74.2 mg)

According to the same experimental protocol as that described in the previous Example, the reaction is carried out at 110° C. and is stopped, this time after 48 hours, and the polymer is analysed.

The conversion into monomer is 74.4%.

The conversion into xanthate is 100%.

$M_n$ equals 6500 g/mol.

$M_w/M_n$ equals 1.14.

By way of comparison, a reaction carried out under the same initial conditions of temperature and concentration, the xanthate of the prior art (ethyl a-(O-ethylxanthyl)-propionate) (or O-ethyl S-(1-methoxycarbonylethyl)dithiocarbonate) leads to a polymer having a polydispersion index close to 2.

EXAMPLE 5

Polymerisation of Vinyl Acetate in the Presence of Xanthate IAa (III)

There are introduced into a Carius tube:
17.4 mmol of vinyl acetate (1.5 g)
0.22 mmol of xanthate IAa (89.8 mg)
0.013 mmol of AIBN (2.1 mg).

According to the same experimental protocol as that described in the previous Example, the reaction is carried out at 80° C., then stopped, this time after 8 hours. The polymer is then analysed.
The conversion into monomer is 11.3%.
The conversion into xanthate is 100%.
$M_n$ equals 1300 g/mol.
$M_w/M_n$ equals 1.17.

EXAMPLE 6

Polymerisation of Styrene in the Presence of Xanthate IAa (IV)

There are introduced into a Carius tube:
43.2 mmol of styrene (4.5 g)
0.184 mmol of xanthate IAa (76 mg)

According to the same experimental protocol as that described in Example 1, the reaction is carried out at 110° C. and is stopped, this time after 48 hours, and the polymer is analysed.
The conversion into monomer is 71.3%.
The conversion into xanthate is 100%.
$M_n$ equals 16200 g/mol.
$M_w/M_n$ equals 1.13.

EXAMPLE 7

Synthesis of a polystyrene-b-ethyl polyacrylate di-block copolymer

According to the same experimental protocol as that described in Example 1, the reaction is carried out at 80° C., and is stopped, this time after 10 hours, and the polymer is analysed.
3 g of polystyrene IV
1.85 g (18.5 mmol) of ethyl acrylate
3 mg of AIBN (0.018 mmol)
5 ml of toluene
The conversion into monomer is 87.3%.
$M_n$ equals 23700 g/mol.
$M_w/M_n$ equals 1.17.

EXAMPLE 8

Synthesis of a polystyrene-b-t-butyl polyacrylate di-block copolymer

According to the same experimental protocol as that described in Example 1, the reaction is carried out at 80° C. and is stopped, this time after 10 hours, and the polymer is analysed.
1 g of polystyrene II
2.96 g (23 mmol) of t-butyl acrylate
2.5 mg of AIBN (0.015 mmol)
5 ml of toluene The conversion into monomer is 91%.
$M_n$ equals 21100 g/mol.
$M_w/M_n$ equals 1.19.

The invention claimed is:

1. Polymer composition that can be obtained by the method comprising bringing into contact with one another an ethylenically unsaturated monomer, a source of free radicals and a compound of formula (IA), (IB) or (IC):

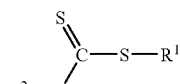

(IA)

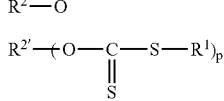

(IB)

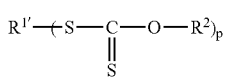

(IC)

in which:
  $R^2$ and $R^{2'}$, which may be identical or different, represent a group of the formula:

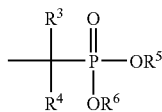

in which:
  $R^3$ and $R^4$, which may be identical or different, are selected from the group consisting of a halogen group, $-NO_2$, $-SO_3R$, $-NCO$, $CN$, $R$, $-OR$, $-SR$, $-NR_2$, $-COOR$, $O_2CR$, $-CONR_2$, $-NCOR_2$, and $C_nF_{(2n+1)}$ with n being from 1 to 20,
  in which the groups R, which may be identical or different, represent H or a group selected from the group consisting of:
    alkyl,
    alkenyl,
    alkynyl,
    cycloalkenyl,
    cycloalkynyl,
    aryl, optionally fused to an aromatic or non-aromatic heterocycle,
    alkaryl,
    aralkyl, and
    heteroaryl,
  which are optionally substituted by one or more identical or different groups selected from the group consisting of halogen, $=O$, $=S$, OH, alkoxy, SH, thioalkoxy, $NH_2$, mono- or di-alkylamino, CN, COOH, ester, amide, $C_nF_{2n+1}$, and/or optionally interrupted by one or more atoms selected from the group consisting of O, S, N, and P,
    or a heterocyclic group optionally substituted by one or more groups as defined above,
  or $R^3$ and $R^4$, together with the carbon atom to which they are attached, form a group $=O$, $=S$ or a hydrocarbon ring or a heterocycle,
  $R^5$ and $R^6$, which may be identical or different, represent a group as defined above for R,
  or $R^5$ and $R^6$ together form a $C_2$-$C_4$ hydrocarbon chain optionally interrupted by a hetero atom selected from the group consisting of O, S and N, $R^1$ and $R^{1'}$, which may be identical or different, represent a group as defined above for $R^3$ or $R^4$, and p represents an integer from 2 to 10.

2. Polymer composition according to claim 1, which has a polydispersion index of at most 2.

3. Polymer composition according to claim 2, which has a polydispersion index of at most 1.5.

* * * * *